United States Patent [19]

Howell

[11] Patent Number: 5,407,899

[45] Date of Patent: Apr. 18, 1995

[54] ALGAECIDAL AND HERBICIDAL COMPOSITIONS COMPRISING TERPENE WETTING AGENTS

[75] Inventor: Bradford S. Howell, Milwaukee, Wis.

[73] Assignee: Applied Biochemists Inc., Milwaukee, Wis.

[21] Appl. No.: 32,603

[22] Filed: Mar. 17, 1993

Related U.S. Application Data

[63] Continuation-in-part of Ser. No. 959,039, Oct. 9, 1992, abandoned.

[51] Int. Cl.⁶ ............... A01N 25/22; A01N 59/20
[52] U.S. Cl. .................... 504/152; 504/187; 71/DIG. 1; 252/351
[58] Field of Search .......... 504/152, 116, 187; 71/DIG. 1; A01N 25/22, 59/20; 252/351

[56] References Cited

U.S. PATENT DOCUMENTS

| | | | |
|---|---|---|---|
| 2,734,028 | 2/1956 | Domogalla | 504/152 |
| 4,361,435 | 11/1982 | Meyers et al. | 504/152 |
| 4,505,734 | 3/1985 | Freedenthal et al. | 504/152 |
| 4,911,952 | 3/1990 | Doane et al. | 71/DIG. 1 |

OTHER PUBLICATIONS

*The Farm Chemicals Handbook* "Cide-Kick", "Cide-Kick II" p. C63, 1987.

Primary Examiner—Peter O'Sullivan
Assistant Examiner—S. Mark Clardy
Attorney, Agent, or Firm—Kane, Dalsimer, Sullivan, Kurucz, Levy, Eisele and Richard

[57] ABSTRACT

The combination of surfactant carrier mixture with an aqueous copper complex in emulsified form provides rapid algaecidal and herbicidal action. The composition is of particular use in running water systems.

5 Claims, No Drawings

ALGAECIDAL AND HERBICIDAL COMPOSITIONS COMPRISING TERPENE WETTING AGENTS

CROSS-REFERENCE TO RELATED APPLICATION

This is a Continuation-In-Part of our U.S. patent application Ser. No. 959,039 filed Oct. 9, 1992 and now abandoned.

BACKGROUND OF THE INVENTION

1. Field of the Invention

The present invention relates to a composition active as an algaecide and a herbicide. In particular, the present invention relates to a composition for use in aquatic environments to control weeds and algae.

2. Brief Description of Related Art

Aquatic environments, such as rivers, canals and ponds, are frequently subject to excessive plant growth which blocks the flow of water and leads to stagnation. As fertilizers and growth promoters wash in to the water from agricultural land, the problem becomes more severe as plant growth increases.

Other aqueous environments, such as swimming pools, shower rooms and storage tanks are often polluted by algal growth which affects the color of the water and can be harmful to water users. Growth in fishponds can be particularly harmful due to the toxic nature of some algae.

The prior art shows that plant and algae growth can be restricted by the use of copper ions. However, such treatment methods are often unsuited for use in flowing water systems.

Copper sulfate has been used for algae control. It is granular and generally applied as such, although it can be dissolved in water and applied as a solution. However, there are problems associated with the use of copper sulfate since the chemical is not stable in water. When applied, copper ions react with carbonates present in the water to produce the insoluble copper carbonate salt which precipitates out of solution. In this form, the copper is no longer bioavailable and so will not control weeds or algae. To overcome this, large doses of copper sulfate are used to compensate for the conversion to copper carbonate. However, over an extended period of time, it is envisaged that accumulated deposits of precipitated carbonate which settle in the mud on the bottom of streams, ponds, irrigation systems and the like may have detrimental effects on the environment. Furthermore, copper sulfate, when used at its maximum legally permissible usage level, will not destroy pondweed.

The use of copper in complexed form has also been proposed. U.S. Pat. No. 2,734,028 discloses a complex formed between copper sulfate and alkanolamines. The copper ions remain in solution even in the presence of carbonates. However, the complex breaks down during storage and when diluted loses its effectiveness.

U.S. Pat. No. 3,930,834 discloses chelated copper ions. Copper compounds are reacted with acid to dissociate copper ions. These are then chelated with, e.g. alkanolamine, tertiary amine and carboxylic acid. The copper remains soluble over a longer period of time than when applied as simple copper sulfate and is more bioavailable to the algae and plants.

However, chelated copper is still not satisfactory in flowing irrigation systems since, even when used at its maximum legally permissible usage level, it tends to be rapidly diluted out before it is able to kill the target algae. Furthermore, the maximum legally permissible usage level is not sufficient to kill pondweed.

Other non-copper based systems are known. For example 2-propenal is used to control weeds and algae in flowing irrigation systems. However, it is highly flammable and toxic. Severe restrictions have been placed upon its use. Herbicides such as Aquathol TM and diquat control aquatic weeds but there are restrictions on the use of such treated water for irrigation.

There is therefore a need for a system which is effective as an algaecide and herbicide in flowing water systems, which satisfies environmental controls and which is safe for fish and use in irrigation supplies.

SUMMARY OF THE INVENTION

The invention comprises an environmentally acceptable carrier composition for formulating emulsions of aqueous solutions of copper coordination complexes, which comprises; a mixture of surfactants obtained from admixture of A. an emulsifying proportion of an emulsifier;
B. a stabilizing proportion of a non-ionic solvent for the copper coordination complex; and
C. a surface-tension reducing proportion of a wetting agent.

The carrier composition is useful to formulate herbicide and algaecide emulsion compositions, having as an active ingredient a copper coordination complex. The carrier composition enhances delivery of copper ions to plant cells and is a rapid acting carrier formulation, particularly useful in flowing water systems.

DETAILED DESCRIPTION OF THE PREFERRED EMBODIMENTS OF THE INVENTION

The carrier compositions of the invention are oils, mixtures of certain specified surfactants.

The term "surfactant" as used herein is a contraction of "surface-active agent" and is a broadly descriptive term used to describe a chemical compound which is (1) soluble in at least one phase of a system, (2) has an amphipathic structure, (3) the molecules of which form oriented monolayers at phase interfaces, (4) exhibits an equilibrium concentration as a solute at a phase interface, greater than its concentration in the bulk of the solution, (5) forms micelles when the concentration as a solute in solution, exceeds a characteristic limiting value and (6) exhibits some combination of the functional properties of detergency, foaming, wetting, emulsifying, solubilizing and dispersing. The surfactants for combination in the oil carriers of the present invention are chosen for their primary functions as emulsifiers, solvents and wetting agents. They may also function as oil phase contributors and as emulsion stabilizers. In the carrier described herein, the formulation with a copper complex is shown to maintain the copper complex in solution for optimal periods of time, to enhance bioavailability of the copper ions and to promote uptake of the copper ions by algae and higher forms of aquatic plant life.

Surfactants which are primarily emulsifying agents (A) for use in aqueous (oil-in-water or water-in-oil) emulsions are generally well known; see for example the Kirk-Othmer Encyclopedia of Chemical Technology, Second Edition, Vol. 8 (Emulsions). The emulsifiers employed in the preparation of the carrier compositions of the invention are anionic emulsifiers. Representative of anionic emulsifying agents are surface active compounds which contain an organic hydrophobic group containing from about 8 to 26 carbon atoms and preferably from about 10 to 22 carbon atoms in their molecular structure; and at least one water-solubilizing group selected from the group consisting of sulfonate, sulfate and carboxylate so as to form a water-soluble surfactant.

Examples of anionic surfactants include soaps, such as, the water-soluble salts (e.g., the sodium, potassium, ammonium and alkanol-ammonium salts) of higher fatty acids containing from about 8 to 20 carbon atoms.

Other anionic emulsifiers are the alkane sulfonates including long chain alkane sulfonates and long chain hydroxyalkane sulfonates. Also the sulfated ethoxylated higher fatty alcohols of the formula $RO(C_2H_4O)_m$-$SO_3M$, wherein R is a fatty alkyl of from 10 to 22 carbon atoms, m is from 2 to 6 (preferably having a value from about 1/5 to ½ the number of carbon atoms in R) and M is a solubilizing salt-forming cation, such as an alkali metal, ammonium, lower alkylamino or lower alkanolamino, or higher alkyl benzene sulfonate wherein the higher alkyls of 10 to 15 carbon atoms are present. The proportion of ethylene oxide in the polyethoxylated higher alkanol sulfate is preferably 2 to 5 moles of ethylene oxide groups per mole of anionic emulsifier, with three moles being most preferred, especially when the higher alkanol is of 11 to 15 carbon atoms.

In a preferred embodiment carrier composition of the invention, a non-ionic emulsifying agent is included as an auxiliary ingredient to assist in stabilizing the emulsion to be formed with the aqueous copper compound solution. Representative of such non-ionic emulsifying agents are the condensation products of ethylene oxide and a lipophile donor compound such as a higher fatty alcohol, preferably having 10 to 18 carbon atoms. Particularly preferred are the ethylene oxide condensation products of alkyl phenols having 5 to 12 carbon atoms in the alkyl groups. Illustrative of the latter are the ethoxylated octylphenol and nonylphenol in which the ethylene oxide content is within the range of from 2 to 30 moles per mole of alkylphenol.

When used, the auxiliary non-ionic emulsifier is advantageously present in a weight proportion of from about 1 to 10 percent by weight of the anionic emulsifier.

Preferred emulsifiers for use in the carrier compositions of the present invention are the fatty acids, particularly fatty acids having from about 12 to about 22 carbon atoms, inclusive. Included are a wide variety of fatty acids that are naturally occurring mixtures of monounsaturated and polyunsaturated fatty acids. Exemplary of monounsaturated acids are: oleic acid, elaidic acid and palmitoleic acid. Examples of polyunsaturated acids are: linoleic acid and linolenic acid. Mixtures of both monounsaturated acids and polyunsaturated acids are exemplified by tall oil fatty acids and soybean fatty acids, each of which contains less than about 10% conjugated unsaturation and having chain lengths of not less than 12 carbon atoms, usually between 16 and 22 carbon atoms.

Another class of preferred anionic emulsifier found particularly useful as a surfactant component of the carrier compositions of the invention are the sulfonates of formula:

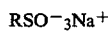

wherein R is a hydrocarbyl group. Representative of such sulfonates are the sulfonates illustrated by sodium xylene sulfonate, sodium lauryl sulfate and the like.

The carrier composition of the invention may comprise one or more surfactant emulsifying agents, and most preferably includes a combination of fatty acids with aryl or alkyl sulfonates.

The emulsifying agent is used in the carrier compositions of the invention in an emulsifying proportion, i.e.; in a proportion sufficient to emulsify the aqueous solution of copper compound to be carried. In general, an emulsifying proportion will be within the range of from about 10 to 40 percent by weight of the total carrier composition.

A solvent (B) for stabilizing the copper complex (to be added to the carrier compositions of the invention) in solution may be any of those used in the preparation of the complex itself. These solvents must be non-ionic or anionic in order to be compatible with the emulsifying agent ingredients. Representative stabilizer solvents are water-soluble anionic surfactant compounds such as the ammonium and substituted ammonium (such as mono, di and tri-ethanolamine), alkali metal (such as, sodium and potassium) and alkaline earth metal (such as, calcium and magnesium) salts or the higher alkyl benzene sulfonates, and higher alkyl sulfates. Preferred is an alkanolamine, such as those containing one or more alkanol groups of from 1 to 10 carbon atoms, inclusive. Representative of most preferred alkanolamines are aminoethylethanolamine, diethanolamine, triethanolamine, dimethylethanolamine, monoethanolamine, diisopropanolamine and the like. The solvent may be used in a stabilizing proportion. In general, a stabilizing proportion is within the range of from about 0.5 to 20 weight percent of the carrier composition.

The wetting agents (C) employed in the carrier compositions of the invention function to enhance penetration of the plant tissues by the copper ions. The wetting agents are in fact "adjuvant surfactants".

The adjuvant surfactant or wetting agent used in the present invention is preferably non-ionic and is preferably a terpene. The term "terpene" as used herein means a hydrocarbon of the general formulae $C_{10}H_{16}$ or $C_{15}H_{24}$ usually found in association with turpentine, citrus extracts, and many other natural essential oils. Most preferred for use in the carrier compositions of the invention is limonene. Limonene is a well known compound, and d,l-limonene occurs in various etherial oils, such as dill, lemon, orange and bergamot. The adjuvant surfactant may be present in the carrier formulation of the invention in an amount sufficient for surface-tension reducing of the aqueous solution containing copper compounds, to be carried by the carrier composition. In general such an amount is within the range of from about 5 to about 70 wt %, more preferably from about 20 to 50 wt % of the carrier composition.

The surfactant mixtures, which are carrier compositions of the invention may be prepared by simple admixture of the three (or more) basic ingredients described above, using conventional liquids mixing apparatus.

The carrier mixtures of the invention may be used to formulate stable emulsions with the aqueous solutions of copper complexes, using conventional emulsification techniques. Whether the formulated emulsion is of the water-in-oil or oil-in-water type is dependent upon the proportions of the oil and water phases. In general, the emulsions of the invention may be of either type, the ratio of carrier to aqueous solution of copper being within the range of from about 0.5:1.0 to 1.0 to 0.5 by volume.

The emulsions are stable for long periods of time, at the end of which they are readily reformed with slight agitation.

The carrier compositions of the invention enhance the up-take of copper ions from aqueous solutions containing copper ions as the herbicidal or algaecidal effective ingredient, by plant organisms. The enhancement is observed in terms of speed of the take-up and quantity of copper ions which penetrate into the physiological system of the organism.

Thus, emulsions are prepared by emulsification of aqueous solutions of ionic copper compounds, with the carrier oil compositions of the invention described above.

The preferred copper complex used in the present invention may be produced in accordance with U.S. Pat. No. 3,930,834, incorporated herein by reference. The complexing agent may be an alkanolamine having at least one alkanol group, a polyethylene glycol of weight average M.Wt 200–5000, a tertiary amine, a carboxylic acid or water soluble salts thereof. Alkanolamines are particularly preferred. A suitable copper complex formulation is the commercially available Cutrine-Plus TM. The preferred level of copper complex used in the emulsion is from about 20 to about 70 wt %, more preferably from about 30 to about 60 wt %. Typically, the preferred amount of elemental copper in the emulsion is from about 1 to about 10 wt %, more preferably from about 2 to 7 wt %. It has been found that the use of an emulsified system in accordance with the present invention at levels below the maximum legally permitted usage levels is effective in clearing both algae and weeds from flowing water systems. The emulsion may be applied to the plants by any method known in the art, e.g. spray application, dripping or injection into the water to be treated.

The following example illustrates the preparation of the compositions according to the present invention, and sets forth the best mode contemplated by the inventor.

EXAMPLE

The following emulsion composition was prepared.

| | Wt % |
|---|---|
| d, l-limonene | 42.5 |
| Tall Oil Fatty Acid[1] | 8.5 |
| Triethanolamine | 2.7 |
| Sodium Xylene Sulfonate | 3.8 |
| Chelated Copper Complex[2] (aqueous) | 42.5 |

[1]Actinol FA-2 (Arizona Chemical); typical tall oil fatty acids comprise about 48.8% oleic acid, 34.3% linoleic acid, 6.4% conjugated linoleic acid, and 8.5% saturated $C_{12}$–$C_{20}$ acids.
[2]Cutrine-Plus (Applied Biochemists Inc)-contains 9.0% elemental copper from mixed copper-ethanolamine complexes (0.11 kg elemental copper per gallon of product).

The d,l-limonene was added to an agitator and the tall oil fatty acid added and mixed until uniform. Triethanolamine was added, followed by sodium xylene sulfonate and mixed until uniform to obtain a carrier composition of the invention. The product is a clear, dark blue liquid emulsion with specific gravity of 1.005.

The final copper content in this formula was approximately 3.5%. an irrigation system size was determined and a sufficient quantity of the emulsified blend applied, by spray, to provide a 1.0 ppm copper residual. Within two hours of the application the pondweed leaf tips and plant tops had turned brown or black indicating rapid kill. In fact, wilting was noted within the first 10 minutes. Algae was also cleared.

A comparative test following the same procedure described above was also carried out, but using the copper complex alone. The comparison shows a much reduced effectiveness in removing pondweed and algae, when the copper complex alone is used.

I claim:

1. A method of controlling the growth of algae and/or plants comprising the step of bringing into contact with the algae and/or plants an emulsion of an aqueous suspension of a copper complex, 5–50 wt % d,l-limonene and an emulsifying agent.

2. An environmentally acceptable agricultural carrier composition which comprises a mixture of surfactants for formulating emulsions of herbicidal and/or algicidal aqueous solutions of copper coordination complexes, said mixture obtained from admixture of
   A. an emulsifying proportion of an emulsifier;
   B. a stabilizing proportion of a non-ionic solvent for the copper coordination complex; and
   C. a surface-tension reducing proportion of a terpene wetting agent.

3. The carrier composition of claim 2, wherein the terpene is limonene.

4. An environmentally acceptable agricultural carrier composition which comprises a mixture of surfactants for formulating emulsions of herbicidal and/or algicidal aqueous solutions of copper coordination complexes, said mixture obtained from admixture of
   A. an emulsifying proportion of a tall oil fatty acid emulsifier in association with sodium xylene;
   B. a stabilizing proportion of triethanolamine solvent for the copper coordination complex; and
   C. a surface-tension reducing proportion of d,l-limonene.

5. A composition for use as an algaecide and herbicide, which comprises;
   an emulsion of a herbicidally and algaecidally effective amount of a copper complex in aqueous solution as the active ingredient; and
   an environmentally acceptable oil carrier, said carrier comprising;
   from about 10 to 40 percent by weight of the carrier of a tall oil fatty acid emulsifier;
   from about 0.5 to 20 percent by weight of the carrier of a solvent for the copper complex; and
   from about 5 to 70 percent by weight of the carrier of a terpene wetting agent.

* * * * *